United States Patent
Wang et al.

(10) Patent No.: US 12,104,171 B2
(45) Date of Patent: Oct. 1, 2024

(54) INDUCTION OF NEURAL PROGENITOR CELLS, OLIGODENDROCYTE PROGENITOR CELLS, AND OLIGODENDROCYTES BY STEM CELL DIFFERENTIATION USING LANDMARK TRANSCRIPTION FACTORS

(71) Applicant: Allele Biotechnology and Pharmaceuticals, Inc., San Diego, CA (US)

(72) Inventors: Jiwu Wang, La Jolla, CA (US); Yuhui Ni, San Diego, CA (US); Yuanyuan Zhao, San Diego, CA (US)

(73) Assignee: Allele Biotechnology and Pharmaceuticals, Inc., San Diego, CA (US)

( * ) Notice: Subject to any disclaimer, the term of this patent is extended or adjusted under 35 U.S.C. 154(b) by 395 days.

(21) Appl. No.: 16/034,910

(22) Filed: Jul. 13, 2018

(65) Prior Publication Data

US 2019/0017019 A1    Jan. 17, 2019

Related U.S. Application Data

(60) Provisional application No. 62/532,246, filed on Jul. 13, 2017.

(51) Int. Cl.

| | |
|---|---|
| C12N 15/63 | (2006.01) |
| C12N 5/074 | (2010.01) |
| C12N 5/079 | (2010.01) |
| C12N 5/0793 | (2010.01) |
| C12N 5/0797 | (2010.01) |
| C12N 15/85 | (2006.01) |

(52) U.S. Cl.
CPC ......... *C12N 5/0623* (2013.01); *C12N 5/0619* (2013.01); *C12N 5/0622* (2013.01); *C12N 5/0696* (2013.01); *C12N 15/8509* (2013.01); C12N 2501/113 (2013.01); C12N 2501/13 (2013.01); C12N 2501/15 (2013.01); C12N 2501/155 (2013.01); C12N 2501/602 (2013.01); C12N 2501/999 (2013.01); C12N 2506/03 (2013.01); C12N 2506/45 (2013.01); C12N 2830/002 (2013.01)

(58) Field of Classification Search
CPC .. C12N 5/0623; C12N 5/0619; C12N 5/0696; C12N 5/0622; C12N 15/8509; C12N 2501/999; C12N 2501/155; C12N 2830/002; C12N 2501/15; C12N 2506/45; C12N 2506/03; C12N 2501/602; C12N 2501/13; C12N 2501/113; C12N 2501/60; C12N 15/63; C12N 15/85; C07H 21/04

See application file for complete search history.

(56) References Cited

U.S. PATENT DOCUMENTS

| | | |
|---|---|---|
| 2002/0068045 A1 | 6/2002 | Reubinoff et al. |
| 2007/0025975 A1 | 2/2007 | Anderson et al. |
| 2010/0317103 A1 | 12/2010 | Cho et al. |
| 2011/0085980 A1 | 4/2011 | Dugas |
| 2013/0302295 A1 | 11/2013 | Wang et al. |
| 2014/0349401 A1 | 11/2014 | Wang |
| 2015/0284681 A1 | 10/2015 | Wernig et al. |
| 2017/0183627 A1 | 6/2017 | Fossati et al. |

FOREIGN PATENT DOCUMENTS

| | | |
|---|---|---|
| WO | WO-2015181253 A1 | 12/2015 |
| WO | WO-2016083458 A1 | 6/2016 |
| WO | WO 2016/187451 A1 | 11/2016 |
| WO | WO2016/207300 A1 | 12/2016 |

OTHER PUBLICATIONS

Wang et al., PNAS, E2885-E2894, 2014, including Supporting Information, 2014.*
Warren et al., Cell Stem Cell, 7: 618-630, Nov. 5, 2010, including Supplemental Information.*
Kim, Jeong Beom, 2017 (US 20170058258 A1, effective filing date, Mar. 7, 2014).*
Pozniak et al., 2010 (PNAS, vol. 107, No. 50, p. 21795-21800).*
Luan, Zuo, 2015 (US 20150093761 A1).*
Balboa et al., "Conditionally stabilized dCas9 activator for controlling gene expression in human cell reprogramming and differentiation," Stem Cell Reports (2015) 5:448-459.
Didovyk et al., "Transcriptional regulation with CRISPR-Cas9: principles, advances, and applications." Current Opinion in Biotechnology (2016), 40:177-184.
Gage, "Mammalian Neural Stem Cells," Science 287:1433-1438 (2000).
Goldman, "Adult Neurogenesis: From Canaries to the Clinic," J. Neurobiology 36:267-286 (1998).
Keyoung et al., "High-yield selection and extraction of two promoter-defined phenotypes of neural stem cells from the fetal human brain," Nature Biotech. 19:843-850 (2001).
Liu K,.et al., "Neuronal Intrinsic Mechanisms of Axon Regeneration." Annu Rev Neurosci. 2011; 34:131-152.
Pincus et al., "Neural Stem and Progenitor Cells: A Strategy for Gene Therapy and Brain Repair," Neurosurgery 42:858-868 (1998).
Pincus et al., "Fibroblast Growth Factor-2/Brain-Derived Neurotrophic Factor-Associated Maturation of New Neurons Generated from Adult Human Subependymal Cells," Ann. Neurol. 43:576-585 (1998).
Pluchino et al., "Injection of Adult Neurospheres Induces Recovery in a Chronic Model of Multiple Sclerosis," Nature 422:688-694 (2003).
Roy et al., "Promoter-Targeted Selection and Isolation of Neural Progenitor Cells from the Adult Human Ventricular Zone," J. Neurosci. Res. 59:321-331 (2000).

(Continued)

*Primary Examiner* — Shin Lin Chen
(74) *Attorney, Agent, or Firm* — Duane Morris LLP (57) ABSTRACT

A novel method of inducing neural progenitor cells, oligodendrocyte progenitor cells, oligodendrocytes from human iPSCs at an unprecedented efficiency and functionality. The core of the invention is the use of experimentally discovered transcription factors at multiple critical differentiation decision points along a pluripotent to ectoderm, neural ectoderm to NPCs to OPCs to oligodendrocytes pathway in a previously unknown manner.

14 Claims, 6 Drawing Sheets

(56) References Cited

OTHER PUBLICATIONS

Roy et al., "In Vitro Neurogenesis by Progenitor Cells Isolated from the Adult Human Hippocampus," Nature Med. 6:271-277 (2000).
Snyder et al., "Multipotent Neural Precursors Can Differentiate Toward Replacement of Neurons Undergoing Targeted Apoptotic Degeneration in Adult Mouse Neocortex," Proc. Natl. Acad. Sci. USA 94:11663-11668 (1997).
Svendsen et al., "New Prospects for Human Stem-Cell Therapy in the Nervous System," Trends Neurosci. 22:357-364 (1999).
Svendsen et al., "Neural Stem Cells in the Developing Central Nervous System: Implications for Cell Therapy Through Transplantation," Progress in Brain Research, Elsevier, 127:13-34 (2000).
Tuszynski MH, Steward O., "Concepts and Methods for the Study of Axonal Regeneration in the CNS," Neuron 2012; 74:777-791.
Vilchez, David, et al. "FOXO4 is necessary for neural differentiation of human embryonic stem cells." Aging Cell Jun. 30, 2013, 12.3: 518-522.
Windrem et al., "Progenitor Cells Derived from the Adult Human Subcortical White Matter Disperse and Differentiate as Oligodendrocytes Within Demyelinated Regions of the Rat Brain," J. Neurosci. Res. 69:966-975 (2002).
Yandava et al., "Global Cell Replacement is Feasible Via Neural Stem Cell Transplantation: Evidence from the Dysmyelinated Shiverer Mouse Brain," Proc. Natl. Acad. Sci. USA 96:7029-7034 (1999).
International Search Report and Written Opinion issued for International Application No. PCT/US18/42027, dated Sep. 19, 2018, 15 pages.
Warren, Luigi, et al. "Feeder-free derivation of human induced pluripotent stem cells with messenger RNA." Scientific Reports 2.1 (2012): 1-7.
Teratani-Ota, Yusuke, et al. "Induction of specific neuron types by overexpression of single transcription factors." In Vitro Cellular & Developmental Biology-Animal 52.9 (2016): 961-973.
Extended European Search Report in EP Application No. 18832965.0, dated Mar. 25, 2021, in 8 pages.
Zhang, Yingsha, et al. "Rapid single-step induction of functional neurons from human pluripotent stem cells." Neuron 78.5 (2013): 785-798.
Sokolik, Cameron, et al. "Transcription factor competition allows embryonic stem cells to distinguish authentic signals from noise." Cell Systems 1.2 (2015): 117-129.
Office Action in JP Counterpart Application No. 2020-501333, dated Jul. 25, 2022, in 3 pages, English translation provided.
Office Action with Search Report in TW Counterpart Application No. 107124367, dated Aug. 30, 2022, in 9 pages, English translation provided.
Xu, Leqin, et al. "Over expression of Mash-1 gene in promoting differentiation of mouse embryonic stem cells into neural cells." Zhongguo xiu fu Chong Jian wai ke za zhi= Zhongguo Xiufu Chongjian Waike Zazhi= Chinese Journal of Reparative and Reconstructive Surgery 29.12 (2015): 1553-1559; English abstract provided.
Lorenz, Carmen, et al. "Human iPSC-derived neural progenitors are an effective drug discovery model for neurological mtDNA disorders." Cell Stem Cell 20.5 (2017): 659-674.

\* cited by examiner

NPC morphology

Pax6 staining

Nestin staining

FIGURE 1

A2B5 staining

O4 staining

FIGURE 5 dCas9-mNeonGreen Fusion dCas9-MyoD Transcription Activation Domain Fusion dCas9-DNMT1 Fusion

FIGURE 6

INDUCTION OF NEURAL PROGENITOR CELLS, OLIGODENDROCYTE PROGENITOR CELLS, AND OLIGODENDROCYTES BY STEM CELL DIFFERENTIATION USING LANDMARK TRANSCRIPTION FACTORS

RELATED APPLICATIONS

This application claims priority to U.S. provisional application Ser. No. 62/532,246, filed on Jul. 13, 2017, which is hereby incorporated by reference.

FIELD OF THE INVENTION

The present disclosure relates to inducing and/or directing the differentiation cascade of pluripotent stem cells to neural progenitor cells to oligodendrocyte progenitor cells to oligodendrocytes through kinetically controlled cell growth processes utilizing specific combinations and ranges of cell density, reagent concentrations, and specific combinations of mRNAs.

BACKGROUND

The recent efforts into the generation and consequent differentiation of human stem cells have changed paradigms concerning the plasticity of cell fate, models for human diseases, and clinical therapeutics. Both embryonic stem cells (ESCs) and induced pluripotent stem cells (iPSCs) made from somatic cells can be differentiated into an increasing list of specific cell types indistinguishable from their corresponding primary cells.

SUMMARY OF THE INVENTION

The present invention provides methods for inducing stem cells and differentiation by modulating cell growth kinetics and associated parameters whereby specific combination of cells density, reagent concentrations, and combinations of mRNAs are used to control the direction of the differentiation/induction. In one aspect, one utility of the current disclosure is a newly developed protocol that provides neural progenitor cells (NPCs), and oligodendrocyte progenitor cells (OPCs), which can become functional and mature oligodendrocytes, as well as directly provide oligodendrocytes for therapies involving various types of myelin sheath-related diseases and injuries.

The present disclosure provides differentiation methods that utilize highly efficient and well-controlled expression of master control genes or key transcription factors in tissue specific differentiation. More specifically, these factors are introduced into pluripotent stem cells in the form of properly modified and purified mRNA molecules demonstrated through the present disclosure.

In one aspect, the present disclosure provides a method of inducing cell differentiation comprising: utilizing key cell fate factors and fusions between conventional transcription factors (TFs) with transactivation domains, optimized for directing stem cells towards different cell types; introducing these factors as synthetic messenger RNA (mRNA) into cultured pluripotent stem cells at the preferred density by methods that results in the appropriate levels of transgene expression; and maintaining cells under optimized conditions to result in high efficiency of specific differentiation whereby the pluripotent state or progenitor state of stem cells or progenitor cells is induced towards a specific lineage or tissue cell type.

In another aspect, the disclosure provides methods for changing the pluripotent state or progenitor state of stem cells or progenitor cells towards a specific lineage or tissue cell type, comprising at least one of: generating stem cells expressing critical cell fate genes (collectively referred as stem cells), including key cell fate factors and fusions between conventional transcription factors (TFs) with trans-activation domains, optimized for directing stem cells towards different types of cells; introducing these factors as synthetic messenger RNA (mRNA) into cultured pluripotent stem cells at the preferred density by methods that result in appropriate levels of transgene expression; maintaining cell under optimized conditions to result in high efficiency of specific differentiation.

In another aspect disclosed herein are methods for inducing differentiation of an induced pluripotent stem cells (iPSCs) and/or embryonic stem cells (ESCs) into neural progenitor cells (NPCs) where the method includes the steps of:
 a) plating iPSCs and/or ESCs on coated, non-tissue treated culture plates;
 b) transfecting the cells of step a) with mRNA encoding one or more cell-fate factors as individual mRNA or combined mRNA; and
 c) culturing said iPSCs and/or ESCs of step b) until the cells differentiate to NPCs.
 d) when larger number of NPCs are needed, the NPCs from c) can be expanded by transferring the cells to uncoated, ultra-low attachment conditions so that they grow in suspension.

In an embodiment of this aspect, the cell fate factors of step b) are selected from the group consisting of one or more of Ngn2, Pax6, Sox2, Brn2 and FoxO family factors as individual mRNA or combined mRNA transfection. In some embodiments the amount of RNA transfected is about 10 ng-about 200 ng or about 20 ng-about 200 ng per well of a 6-well plate or proportionally adjusted, based on area of the vessel or the volume of the culture media amount, when using other type of plates or culture flask. In some embodiments, the transfection is repeated at least one more time. The transfections can be repeated around 24 hour intervals. In another embodiment, the cell-fate factors can be fused to a transactivation domain, such as, without limitation, MyoD or VP16. In some embodiments, the cells of step c) are cultured until the cells express one or more of the cell-fate factors of step c). Determination of whether a cell-factor is expressed can be done using, without limitation, immunoassays and/or qt-PCR. In still other embodiments, one or more of SB43542, LDN193189, and PD173074 can optionally be added to the cells of step c). In some embodiments, the culture conditions of steps a)-c) are in an oxygen concentration of about 2% to about 6%. In an embodiment of the disclosure, the medium used in steps a)-c) is selected from minimal essential media-alpha (MEMa), Dulbecco's Modified Eagle Medium:Nutrient Mixture F-12 (DMEM/F12), or DMEM with B27 supplement. The medium may also contain other components, such as Knock Out Serum Replacement (KSR), and one or more of bFGF, N2 or B27, BSA or HSA. In another embodiment, the culture vessel is coated with Matrigel and/or PLO-Laminin. In an embodiment of the method, the iPSCs and/ESCs of step a) are seeded at about $0.75 \times 10^5$ cells to about $1.5 \times 10^6$ cells/well in a six-well plate. Other sized culture vessels can be used. The seeding density for culture vessels other than six-well plates can be determined based on using about 70,000 cells-about 14,000,000 cells and dividing the cell numbers by the growth area of the culture vessel, for example, as shown in Table 2. In some embodiments, the cells of step c) are cultured for about 3 to about 10 days when cells have an astrocyte-like or neuron-like morphology. After about 3 to about 10 days, close to about 100%, but above about 75% of the cells will have a characteristic morphology of an NPC cell. In some embodiments, about 40-60% of the cells will have a characteristic morphology of an NPC cell. If lower than about 40% of cells have a characteristic morphology of an NPC-cell, then cell sorting can be used to isolate cells. Further culturing using a suspension culture system allows for further selection. In some embodiments, confirmation of an NPC can be shown by expression of one of the cell-fate factors, such as Pax6.

Another aspect of the disclosure are methods for generating oligodendrocyte progenitor cells (OPCs) from NPCs where the method includes the steps of:
 a) plating NPCs on coatedculture vessels in medium;
 b) transfecting the cells of step a) with mRNA encoding one or more cell-fate factors as individual mRNA or combined mRNA to differentiate neural progenitor cells to oligodendrocyte progenitor cells;
 c) culturing the cells of step c) until the morphology of the NPCs change to the morphology of an OPCs;
 d) when larger number of OPCs are needed, the OPCs from c) can be expanded by transferring to uncoated, ultra low attachment so that they grow in suspension.

In an embodiment of this method, in step a) the wells of a six-well plate are seeded at about $0.75 \times 10^5$ cells/well to about $1.5 \times 10^6$ cells/well. Other sized culture vessels can be used. The seeding density for culture vessels other than six-well plates can be determined based on using about 70,000 cells-about 14,000,000 cells and dividing the cell numbers by the growth area of the culture vessel, for example, as shown in Table 2. In another embodiment, the mRNA used for transfection in step b) encodes for cell-fate factors selected from one or more of the group consisting of Oligo2, NKX2.2, SOX10, and Oligo1 mRNA individually or in combination. In another embodiment, the dose for the transfection in step b) is about 20 ng/per—about 100 ng cell-fate factor when using a six-well culture plate or proportionally adjusted, based on area of the vessel or the volume of the culture media amount, when using other type of plates or culture flask. In another embodiment, after the first transfection, the transfection is repeated at least two more times at doses of mRNA of about 10 ng/cell-fate factor to about 200 ng/cell-fate factor when using a six-well culture plate or proportionally adjusted, based on area of the vessel or the volume of the culture media amount, when using other type of plates or culture flask. In another embodiment, the culture vessel plates are coated with Matrigel and/or PLO-Laminin. In another embodiment, the medium used for steps a)-c) is selected from DMEM/F12, DMEM, and MEMa. In some embodiments, the medium is supplemented with one or more of KSR, ascorbic acid, SAG, PDGF, HGF, IGF1, T3, insulin, RA, B27, CAMP, and/or biotin. In an embodiment of the method, the culture conditions of steps a)-d) are in an oxygen concentration of about 2% to about 6%. In another embodiment, the cells in step c) are cultured for about 4 to about 20 days until cells with the morphologic characteristics of an OPC are observed. In another embodiment, OPC generation can be confirmed based on bipolar morphology and/or expression of one of the cell-fate factors. After about 4 to about 20 days, close to about 100%, but above about 75% will have a characteristic morphology of an OPC cell. In some embodiments, about 40-60% of the cells will have a characteristic morphology of an OPC cell. If lower than about 40% of cells have a characteristic morphology of an OPC-cell, then cell sorting can be used to isolate cells. Further culturing using a suspension culture system allows for further selection. In some embodiments, confirmation of an OPC can be shown by expression of one of the cell-fate factors, such as Oligo2 or Sox10.

In another aspect of the disclosure are methods for generating oligodendrocytes from OPCs based on the following steps:
 a) plating OPCs on coated, culture vessels in medium; and
 b) culturing the cells of step a) until cells appear with branched cell processes and/or produce myelin basic protein (MBP).

In an embodiment of this method, the medium used for steps a)-c) is selected from DMEM/F12, DMEM, or MEMa. The medium can be supplemented with one or more of the medium supplements selected from the group consisting of KSR, ascorbic acid, N2, B27, biotin, CAM, T3, and insulin. In another embodiment, the OPCs of step a) are seeded at about $0.75 \times 10^5$ cells to about $1.5 \times 10^6$ cells per well using a 6-well plate. The seeding density for culture vessels other than six-well plates can be determined based on using about 70,000 cells-about 14,000,000 cells and dividing the cell numbers by the growth area of the culture vessel, for example, as shown in Table 2. In another embodiment, the cells of step b) are cultured for about 7 to about 30 days at which time cells with branched cell processes will be present. In another embodiment, the cell culture vessels in step a) are coated with Matrigel and/or PLO-Laminin.

In another aspect of the disclosure are methods for inducing differentiation of stem cells, such as iPSCs or embryonic stem cells into NPCs, OPCs, oligodendrocytes sequentially or directly using the following steps:
 a) plating iPSCs and/or ESCs on a coated culturing vessel, wherein the iPSCs and/ESCs are seeded at about $0.75 \times 10^5$ cells to about $1.5 \times 10^6$ cells per well of a 6-well plate, or proportionally adjusted if other culture vessels are used, in medium comprising containing minimal media-alpha (MEMa), or Dulbecco's Modified Eagle Medium: Nutrient Mixture F-12 (DMEM/F12), or DMEM with B27 supplement all with knock out replacement serum (KSR);
 b) transfecting the cells of step a) with mRNA encoding cell fate factors selected from the group consisting of one or more of Ngn2, Pax6, Sox2, Brn2 and FoxO family factors as individual mRNA or combined mRNA transfection;
 c) culturing said iPSCs and/or ESCs of step b) until the cells differentiate to NPCs.
 d) isolating the NPCs from step c):
 e) plating NPCs on coated cell culture vessels, wherein the NPCs are seeded at about $0.75 \times 10^5$ cells to about $1.5 \times 10^6$ cells well of a 6-well plate, or proportionally adjusted if other culture vessels are used, in medium comprising MEMa, or DMEM/F12, or DMEM, all with KSR and one or more of the medium supplements selected from the group consisting of ascorbic acid, SAG, PDGF, HGF, IGF1, T3, insulin, RA, B27, CAMP and biotin;
 f) transfecting the cells of step e) with one or more of the group consisting of Oligo2, NKX2.2, SOX10, and Oligo1 mRNA individually or in combination using transfection reagents;

g) repeating the transfection of step e) at least two more times at doses of about 10 ng to about 200 ng (per well in 6-well plate);

h) culturing the cells of step g) until the morphology of the cells change from the morphology of an NPC cell to an OPC cell;

i) isolating the OPCs from step h);

j) plating the isolated OPCs from step j) onto coated cell culture vessels, wherein the OPCs are seeded at about $0.75 \times 10^5$ cells to about $1.5 \times 10^6$ cells well of a 6-well plate, or proportionally adjusted if other culture vessels are used, in medium comprising MEMa, or DMEM/F12, or DMEM, all with KSR and one or more of the medium supplements selected from the group consisting of ascorbic acid, N2, B27, biotin, Cam, T3, and insulin; and K) culturing the cells for at least about 1 week until oligodendrocytes cells appear with tree branch-looking processes and/or produce myelin basic protein (MBP).

In another aspect of the invention, the starting cells for the methods disclosed herein are are harvested from the recipient, such as from a body fluid or tissue.

Another aspect of the disclosure are the NPCs, OPCs, and oligodendrocytes obtained from the disclosed methods. In an embodiment of this aspect, the cells can be used as pharmaceutical compositions to treat a disease, disorder or malformation. Such diseases, disorders and malformations can include, without limitation a neurodegenerative condition such as an acute neurodegenerative condition, such as a brain trauma (focal or diffuse brain trauma), spinal cord trauma or peripheral nerve trauma e.g., resulting from physical or chemical burns, deep cuts or limb severance, cerebrovascular insufficiency. In other embodiments, it is a chronic or progressive neurodegenerative condition, such as Parkinson's disease, Alzheimer's disease, Huntington's disease, amyotrophic lateral sclerosis, tumor, or chronic peripheral nerve injury, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Sträussler-Scheinker disease, Kuru and fatal familial insomnia). In still other embodiments, it is a disease associated with demyelination, such as multiple sclerosis, acute disseminated encephalomyelitis, neuromyelitis optica, transverse myelitis, chronic inflammatory demyelinating polyneuropathy, Guillain-Barré syndrome, central pontine myelinosis, inherited demyelinating diseases such as leukodystrophy, Charcot-Marie-Tooth disease and Canavan disease.

BRIEF DESCRIPTION OF THE DRAWINGS

Aspects of the present disclosure will now be described in relation to the drawings as described below.

DETAILED DESCRIPTION

When describing the present disclosure, all terms not defined herein have their common meanings recognized in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

iPSCs show particular potential in the field of personalized medicine because of the unlimited availability of cells, the noninvasiveness of the procedure to obtain the cells, and the potential to be immune-matched for each treatment to individual patients, granting freedom from immunosuppressive drugs.

Cell replacement therapies offer new hope to treat various injuries, and to treat or prevent various human diseases that previously had no real treatment. For example, spinal cord injuries resulting from accidents, other spinal cord conditions such as multiple sclerosis and various leukodystrophies, are currently managed in hospitals without means to amend the loss of the myelin sheath and its neurological functions. Finding a reliable supply of NPCs, OPCs, and oligodendrocytes remains a significant hurdle to overcome. Although there is a clear need of cells that can help sufferers of spinal cord injuries or spinal diseases, the efforts of researchers and companies has not to date provided methods that can generate fully functional oligodendrocytes with mature morphology. Even if NPCs or OPCs are to be used to treat spinal cord conditions, the ability of these precursors to give mature, functional, normal oligodendrocytes is still a critical measure of their potential to be used for medical treatment.

Most current protocols for deriving functional tissue cells from pluripotent stem cells require the use of combinations of growth factors, hormones, cytokines, signal peptides and other intercellular signal molecules (collectively referred to as "growth factors" for simplicity in this disclosure) at each step along a differentiation cascade to produce medically applicable NPCs, OPCs or oligodendrocytes. Unfortunately, when supplied as purified polypeptides, growth factors are generally expensive, unstable, and inconsistent from batch-to-batch, making them difficult to use. Additionally, because growth factors function in a highly specific yet combinatorial manner, each stage of differentiation is dictated by a different set of growth factors, which is difficult and costly to optimize. As disclosed herein, NPCs, OPCs, and oligodendrocytes can be achieved at very high efficiency and at lower costs without using large amount of growth factors by combining mRNA at critical fate changing points at the right dose and delivery conditions.

To alleviate the burden of cost and inconsistency, those of skill in the art often resort to finding small molecules that can influence signal pathways as an agonist or antagonist of growth factor receptors, thereby in a way substituting for growth factors. Small molecules are typically much cheaper than growth factors. However, one major disadvantage of small molecules is the non-specific effects they may exert on unintended targets, such as cell membrane-bound receptors, intracellular organelles, or genomic components, etc. The present disclosure also provides novel methods of achieving cell fate determination with no or reduced use of small molecules.

There so far has been very limited information, if any, on how to differentiate pluripotent stem cells all the way to terminal oligodendrocytes, possibly because a detailed road map with growth factors and small molecules to guide differentiating cells through each stage has yet to be drawn through tedious experimentation. Because mRNAs are more specific, through encoding functional proteins, in directing cellular and developmental events, the disclosed method is much more robust than any known methods in creating primary oligodendrocyte-like cells, paving a way for human therapies in treating spinal cord injuries, defects, diseases, and myelin sheath and other related health problems.

Another key component of a typical differentiation protocol is the media for culturing cells, which may be composed of nutrients (lipids, amino acids, carbohydrates, vitamins, etc.), proper concentrations of salts, pH buffering agents, critical elements, and common protein factors such as insulin or serum albumin. Different types of cells have different requirements of nutrients and media components and is further complicated by cell type specific growth factors and small molecules for signaling. Therefore, a special "differentiation medium" is often painstakingly tested by removing or adding one component at a time. A major benefit of the current disclosure is the simplicity of establishing differentiation medium through use of properly supplied mRNAs of differentiation-directing genes. Optimal combination of mRNAs and appropriate medium, however, can further benefit the process and is an integral part of the current disclosure.

In clinical applications of stem cell derived tissue cells, most components of the established differentiation media require individual certification under the current good manufacturing practice (cGMP) regulations; for example, growth factors need to be produced by special procedures and require individual certification. Likewise, some small molecules added to specific differentiation media are produced through special chemical synthesis processes that vary in purity, stability, and toxicity. In the field of stem cell cultures, some previously published protocols also rely on animal products such as serum or Matrigel. Another incentive behind the current disclosure is to create a new method that is primarily based on a single type of molecule suitable to uniform certification and quality control processes.

Described herein are processes that involve how cell density and rate of division can be managed to achieve desired differentiation results. Further disclosure teaches the optimization of timing, order of addition, RNA doses and ratios among different RNAs during transfection of RNAs, and their duration or number of repeats. The disclosure further relates to the choices of surface of culture vessels and environmental conditions such as oxygen concentration. The invention further includes methods of selection of desired cells or enhancement of their percentage in the overall population, and methods of cryopreservation and re-culture of differentiated cells.

The concept of "master control" gene, i.e., one key gene (typically a transcription factor gene, sometimes a small number of genes working together) can decide the fate of cells and tissues and eventually the formation of an entire organ during development, has been generally accepted based on studies in muscle (MyoD), eye (Pax6), and other fields of developmental biology. Shinya Yamanaka's discovery that differentiated cells can be reverted to a pluripotent state by the expression of a select group of transcription factors expressed in stem cells, through viral delivery, demonstrated the power of a small number of key transcription factors in driving cells through a lengthy, multi-stage fate change. Work by other groups on iPSC generation expanded the choices of reprogramming factors and showed that some variations can be tolerated in transcription factor choices for the purpose of reprogramming. In Yamanaka's original work, expression of the reprogramming factors was achieved through the application of viral vectors which integrate into the genome because prolonged expression of these factors is required to effect cell transformation. The attendant modification of the genome represents an important hurdle to therapeutic application of iPSCs, while the possibility of reactivated expression from integrated viral cassettes is a concern even for in vitro studies. The application of mRNA transfection to reprogramming as most recently disclosed by the current inventor group is particularly appealing as this system allows the expression of reprogramming cocktails and even individual component factors to be modulated in short time frames simply by changing which transcripts are added to the cell culture media. Once transfection of a particular factor is terminated, ectopic expression within the target cells ceases quickly due to the rapid decay of mRNA in the cytoplasm. Even though mRNA does not persist in the target cell, its ability to be directly translated in the cytoplasm, without the need of rate-limiting nuclear translocation as in the case of transfected DNA and integrating viral vectors, more than compensate for mRNA's short half-life to result in highly efficient expression but well within a small-time window, which is critical for cell fate determination.

Long-lasting DNA vectors, such as episomal plasmids, when used for cell fate alteration, require weaning to reduce any risk of random genomic integration. RNA viruses or virus-derivatives, such as the Sendai virus or Venezuelan equine encephalitis (VEE) virus, even after being a modified to a noninfectious RNA replicon, still carries viral elements, prone to recombination with viral elements hidden in the host genome. It is always difficult to be completely sure that the cells are rid of the viral vectors without tedious finding of proof in the form of negative data. The current disclosure discloses multiple inventive steps aimed at applying the advantages of mRNA-based cell fate determination to directed differentiation. In summary, the current disclosure teaches a single or multiple rounds of ectopic transcription factor expression in a streamlined method to direct cell differentiation.

Nonetheless, there are technical barriers to mRNA-based stem cell differentiation. Not all stem cell types and culture media are equally conducive to efficient mRNA delivery, and this is currently an impediment to mRNA-based differentiation. Further, stem cells, particularly most human stem cell lines, are rather difficult to culture without forming transfection-resistant patches. As disclosed herein, pluripotent stem cells can be grown under conditions so that most of the cells can be transfected with mRNAs. In another embodiment, the dose of RNA and transfection reagent (both of which have associated toxicities) are provided to the cells at levels capable of exerting master control gene effects while supporting the viability of the target cells in the face of the pro-apoptotic and cytostatic forces engendered by the cell fate changing process.

Accordingly, in view of the problems associated with the previously known stem cell differentiation procedures, the novel methods, materials, and protocols described herein produce different cell types from iPSCs or embryonic stem cells (ESCs) with improved efficiency of the process and quality of the resultant cells. The current disclosure shows significant improvements through potentiation of the TF mRNA delivered to the target stem cells. The current disclosure also provides novel protocols which support the production of footprint-free tissue cells from human stem cells without the use of feeder cells or any other potentially xeno-contaminated reagents. The new protocols extend the benefits of the modified mRNA and help clear remaining roadblocks to the therapeutic application of stem cell derivation technology.

Given that differentiation from pluripotent to terminally differentiated state often takes multiple steps, requiring a time frame of several weeks to even months, the growth factor-based, stepwise strategy is intrinsically inefficient and tedious. Accordingly, embodiments of the present disclosure fundamentally remove the need for growth factors in guiding generation of neural progenitor cells to oligodendrocyte progenitor cells to oligodendrocytes cells.

More specifically, this disclosure relates to changing the pluripotent state or progenitor state of stem cells or progenitor cells (collectively referred as stem cells) towards a specific lineage or tissue cell type by expressing critical cell fate genes, including key cell fate factors and fusions between conventional transcription factors (TFs) with transactivation domains such as those of MyoD or VP16 and many other commonly known in the field that provide strong transcription activation activities, optimized for directing stem cells towards different types of cells; introducing these factors as synthetic messenger RNA (mRNA) into cultured pluripotent stem cells at the preferred density by methods that result in appropriate levels of transgene expression; maintaining cells under optimized conditions to result in previously unattainable efficiency of specific differentiation. Factors expressed through introduction of mRNA can also include growth factors, cytokines, hormones, signal peptides and other cell fate influencing secreted factors or modifying enzymes. Using similar procedure, microRNAs (miRNAs) or other non-protein-coding RNAs can be introduced into cells under cell state transition in order to direct differentiation because these non-coding RNAs can control or influence TFs, essentially provide the same effects as directly transfecting the TF mRNAs. Furthermore, TFs critical for differentiation as described in the Examples can be activated by using a modified CRISPR-Cas9 system, wherein an engineered Cas9 (e.g. non-cutting Cas9) or other Cas family member proteins are fused to a transcription activation domain (and in some cases transcription repression domain for depressing TFs with opposite effects of desired TFs), a chromatin modifying enzyme or its enzymatic domain, or other epigenetic modifying enzyme or its enzymatic domain, together with guide RNA(s) that direct these action domains to the vicinity of the target TF genes on the chromosome. Disclosed herein are CRISPR-Cas systems for cell differentiation, preferably using only RNA as molecules delivered inside the target cell for the same benefits as described above, except when a DNA molecule is needed as a template to change a genome sequence. Compared to other methods known in the art, the methods disclosed herein dramatically reduce the time, cost, and effort involved in stem cell differentiation into NPCs, OPCs, and oligodendrocytes.

The disclosure herein specifically describes in detail methods of changing the pluripotent state or progenitor state of stem cells or progenitor cells towards a specific lineage or tissue cell type, comprising at least one of: expressing critical cell fate genes, including key cell fate factors optimized for directing stem cells towards different types of cells; introducing these factors as synthetic messenger RNA (mRNA) into cultured pluripotent stem cells at the preferred density by methods that result in appropriate levels of transgene expression; and maintaining cells under optimized conditions to result in high efficiency of specific differentiation.

In certain embodiments, the fully stabilized, expanded human ESCs or iPSCs are provided.

In certain embodiments, there is no need to clear episomes or RNA virus (e.g., Sendai), which can take 10+ passages of iPSCs post-isolation.

In certain embodiments, the process is feeder-free.

In certain embodiments, the process is xeno-free, comprising all synthetic or human reagents and no non-human animal-derived components.

In certain embodiments, the process is footprint-free: having no random integration of DNA into genome (as often happens with episomal DNA constructs).

In certain embodiments, the mRNA's functions may be achieved by using non-coding RNAs (including miRNAs) or a guide-RNA/Cas-fusion system, with the understanding of which TFs' activities are critical for a specific differentiation step disclosed in the Examples below.

In certain embodiments, the process yields a fully-customized genetic background via patient-specific starting tissue and/or genome-editing.

Definitions

As used herein, the term "about" means within 20%, more preferably within 10% and most preferably within 5%. The term "about" when used in the context of days means one, or two days more or less. Thus, if a cell culture is cultured for about 3 to about 10 days, this can mean from 3-10 days, 1 to 12 days or 2 to 11 days.

The term "oligodendrocyte-like cell" is intended to mean a cell sharing features with an oligodendrocyte. Oligodendrocyte-like cells are further defined by morphological characteristics as well as by specific marker characteristics. As induced pluripotent stem cell-derived oligodendrocyte-like cells share similar characteristics (including marker and hormonal characteristics) with primary oligodendrocytes, induced pluripotent derived oligodendrocyte-like cells may be used interchangeably with induced pluripotent stem cell-derived oligodendrocyte, or simply oligodendrocyte.

An "embryoid body" refers to an aggregate of cells derived from pluripotent cells, where cell aggregation can be initiated by any method that prevents the cells from adhering to a surface to form typical colony growth. As used herein, "embryoid body" refers to a three-dimensional spheroid aggregate of pluripotent stem cells, including but not limited to embryonic stem cells derived from the blastocyst stage of embryos from mammalian sources. An embryoid body can be formed from embryonic stem cells derived through any technique generally known in the art, including but not limited to somatic cell nuclear transfer or the reprogramming of somatic cells to yield induced pluripotent stem cells.

As used herein, the term "induced pluripotent stem cells" refers to a pluripotent stem cell derived from a somatic cell (e.g. an adult somatic cell). Induced pluripotent stem cells are similar to embryonic stem cells in their differentiation abilities to form any adult cell types, but are not derived from an embryo, i.e., cells capable of differentiating into multiple cell types that are artificially derived (not naturally derived) from a non-pluripotent cell As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant. In the context of this disclosure, composition would also include differentiated cells generated from the methods described herein, including NPCs, OPCs and oligodendrocyte cells.

As used herein, "culturing" refers to maintaining cells under conditions in which they can proliferate and avoid senescence as a group of cells. "Culturing" can also include conditions in which the cells also or alternatively differentiate.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "differentiate" or "differentiation," refers to the process by which precursor or progenitor cells (i.e., neural progenitor cells) differentiate into specific cell types, e.g., oligodendrocytes.

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes, within its scope, amounts effective to enhance normal physiological function.

As used herein, "expansion" or "expanded" in the context of cells, refers to an increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "integration free iPS cell" refers to an iPS cell that does not contain an exogenous transgene integrated into the genome of the non-pluripotent cell.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart. With respect to NPCs, OPCs, and oligodendrocytes as described herein, isolated means separated from non-differentiated cells and to isolate a pure population of the cells of interest.

As used herein, "concentrated" refers to a molecule, including but not limited to a cell, particular types of cells, polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "diluted" refers to a molecule, including but not limited to a cell, particular types of cells, polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "separated" refers to the state of being physically divided from the original source or population such that the separated compound, cell, agent, particle, or molecule can no longer be considered part of the original source or population.

As used herein, "mammal," for the purposes of treatments, refers to any animal classified as a mammal, including human, domestic and farm animals, nonhuman primates, and zoo, sports, or pet animals, such as, but not limited to, dogs, horses, cats, and cows.

As used herein, "stem cell" refers to any self-renewing totipotent, pluripotent cell or multipotent cell or progenitor cell or precursor cell that is capable of differentiating into multiple cell types.

As used herein, "totipotent" refers cells that can differentiate and give rise to all cells types in an organism, plus the extraembryonic, or placental, cells.

As used herein, "pluripotent" refers to cells that can differentiate and give rise to all of the cell types that make up an organism, including any fetal or adult cell type, except for the extraembryonic, or placental, cells.

As used herein, "multipotent" refers to cells that can develop into more than one cell type, but are more limited than pluripotent cells in the cell types that they can develop into.

As used interchangeably herein, "subject," "individual," or "patient" refers to a vertebrate organism.

As used herein, "substantially pure cell population" refers to a population of cells having a specified cell marker characteristic and differentiation potential that is about 50%, preferably about 75-80%, more preferably about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

As used herein, "pre-differentiation" refers to the process by which precursor or progenitor cells (e.g., pluripotent stem cells) differentiate into intermediate cell types, e.g., neural or oligodendrocyte progenitor cells, which have the potential to differentiate further to final effector cells (e.g. oligodendrocytes).

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, pallative treatment, and partial remediation of a disease, disorder, condition or side effect.

The terms "treating" and "treatment" as used herein refer generally to obtaining a desired pharmacological and/or physiological effect. The effect may be prophylactic in terms of preventing or partially preventing a disease, symptom or condition thereof, and/or may be therapeutic in terms of a partial or complete cure of a disease, condition, symptom, or adverse effect attributed to the disease. The term "treatment" as used herein covers any treatment in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The term "treatment" as used herein refers to both therapeutic treatment and prophylactic or preventative measures. Those in need of treatment include those already with the disorder as well as those in which the disorder is to be prevented.

As used herein, "preventative" refers to hindering or stopping a disease or condition before it occurs, even if undiagnosed, or while the disease or condition is still in the sub-clinical phase.

As used herein, "active agent" refers to a substance, compound, or molecule, which is biologically active or otherwise induces a biological or physiological effect on a subject to which it is administered to. In the context of the present disclosure, the NPCs, OPCs, and oligodendrocytes produced by the methods described herein are an "active agent".

As used herein, "pharmaceutically acceptable carrier" refers to diluent, adjuvant, excipient, or vehicle with which an active agent, chondrocytes of the present disclosure, or composition containing oligodendrocytes of the present disclosure is administered in conjunction with and that is approved by a regulatory agency of the Federal or a state government or listed in the U.S. Pharmacopeia or other generally recognized pharmacopeia for use in animals and/or humans.

As used herein "FoxO" refers to a subclass of the fork head transcription factor family members. For the experiments disclosed herein, mRNA from one or more of the FoxO family members can be used, e.g., FoxO1, FoxO2, FoxO3a, and FoxO4

Unless otherwise defined herein, all technical and scientific terms used herein have the same meaning as commonly understood by one of ordinary skill in the art.

Cell types: Exemplary cell types can include, for example, Ectoderm cells; Neural Progenitor cells; Oligodendrocyte Progenitor cells; Oligodendrocytes.

Examples of suitable surfaces for culture vessels for iPSCs include but are not limited to Vitronetin, E-cadherin, Corning® Synthemax® II or Matrigel; for Neural Ectoderm and Neural Progenitors suitable surfaces include but are not limited to Matrigel, PLO-Lamnin; for Neural Progenitors and Oligodendrocyte Progenitor cells and Oligodendrocytes, suitable surfaces include but are not limited to Matrigel or PLO-Lamnin or Collagen.

In one aspect, an exemplary method for dedifferentiating or reprogramming somatic cells can include the use of any one or more of a synthetic mRNA reprogramming factor selected from Oct4, Sox2, Klf4, cMyc, Nanog, and Lin28 and transactivation domains whereby the somatic cell is reprogrammed or de-differentiated. Methods and compositions for iPSC modulation are described in U.S. patent application Ser. Nos. 13/893,166 and 14/292,317, such iPSCs can be used for the methods described herein. The contents of which are hereby incorporated by reference.

Suspension systems, if possible, are more practical for large-scale production for clinical applications. Therefore, at each stage the protocols have been tested to see whether cells can be expanded well in suspension. In certain embodiments, there are protocols for the use of suspension cell cultures, and low cell-attachment culture plates and vessels that can be used for such suspension cultures.

In certain embodiments, the environmental conditions such as oxygen concentration can be modulated for optimal induction conditions.

In certain embodiments, processes and methods of selection of desired cells or enhancement of their percentage confluence or cell density in the overall cell culture population are provided.

In certain embodiments, methods of cryopreservation of the NPCs, OPCs, or oligodendrocyte-like cells are provided. Some of the differentiated cells may need to be cryopreserved for optimal cell viability during storage. For example, 2.5% HSA with 10% DMSO in culture medium can be used. The cell numbers can be optimized for the further improvement of viability in storage using this application.

Re-culture differentiated cells methods are also provided. Cells can be re-cultured in most culture vessels: e.g., without limitation, T75 flask, T25 flask, 4-well plate, 6-well plate, 8-well plate, 24-well plate, 48-well plate, and 96-well plate. Cells can be re-cultured in different cell density for different applications.

In certain embodiments, the present disclosure also provides methods for managing physical stress on the cells thereby improving viability during handling throughout the differentiation process. Certain types of cells during the differentiation are very small, like iPSCs. These small cells are very sensitive to centrifuge force. For maintenance, these cells can be cultured as colonies and then dissociated as clusters, instead of single cells. For differentiation, if single cells are necessary, one can end the dissociation prior to the cells detaching, remove the dissociation solution, and let the residual dissociation solution further dissociate the cells. This protocol is commonly used in cell culture. iPSCs are very sensitive to excessive centrifuge force. Some types of cells during the differentiation are very sticky, like iPSCs. These cells are very sensitive to sheer force. When handling these cells, a 10 mL pipet was used to avoid use of any small tips and to avoid pipetting the cells up and down repeatedly. Oligodendrocytes have unique cell morphology that includes many branches, processes with abilities to attach to axons. Removing oligodendrocytes from one vessel to another requires delicate manipulation and uncommon skills that the inventors of the current disclosure acquired through trials and tribulations.

The NPCs, OPCs and oligodendrocytes produced through the methods of the present disclosure can be used to treat spinal injuries and other injuries. For example, highly enriched or purified populations of the NPCs, OPCs, and/or oligodendrocytes produced using the methods of the present invention may be used for transplantation into a variety of conditions of brain and spinal cord disease and injury—For background information see (Liu K, et al., "Neuronal Intrinsic Mechanisms of Axon Regeneration." *Annu Rev Neurosci.* 2011; 34:131-152). Tuszynski M H, Steward O., Concepts and Methods for the Study of Axonal Regeneration in the CNS. *Neuron.* 2012; 74:777-791). (Gage, "Mammalian Neural Stem Cells," *Science* 287:1433-1438 (2000), all of which are hereby incorporated by reference in their entireties). (Goldman, "Adult Neurogenesis: From Canaries to the Clinic," *J. Neurobiology* 36:267-286 (1998); Pincus et al., "Neural Stem and Progenitor Cells: A Strategy for Gene Therapy and Brain Repair," *Neurosurgery* 42:858-868 (1998); Svendsen et al., "Neural Stem Cells in the Developing Central Nervous System: Implications for Cell Therapy Through Transplantation," *Prog. Brain Res.* 127: 13-34 (2000); and Svendsen et al., "New Prospects for Human Stem-Cell Therapy in the Nervous System," *Trends Neurosci.* 22:357-364 (1999), which are all hereby incorporated by reference in their entireties). (Snyder et al., "Multipotent Neural Precursors Can Differentiate Toward Replacement of Neurons Undergoing Targeted Apoptotic Degeneration in Adult Mouse Neocortex," *Proc. Natl. Acad. Sci. USA* 94:11663-11668 (1997), which is hereby incorporated by reference in its entirety), and to remyelinate regions of the brain demyelinated in either chemical (Windrem et al., "Progenitor Cells Derived from the Adult Human Subcortical White Matter Disperse and Differentiate as Oligodendrocytes Within Demyelinated Regions of the Rat Brain," *J. Neurosci. Res.* 69:966-975 (2002), which is hereby incorporated by reference in its entirety) or autoimmune demyelination (Pluchino et al., "Injection of Adult Neurospheres Induces Recovery in a Chronic Model of Multiple Sclerosis," *Nature* 422:688-694 (2003), which is hereby incorporated by reference in its entirety). (Yandava et al., "Global Cell Replacement is Feasible Via Neural Stem Cell Transplantation: Evidence from the Dysmyelinated Shiverer Mouse Brain," *Proc. Natl. Acad. Sci. USA* 96:7029-7034 (1999), which is hereby incorporated by reference in its entirety).

In some embodiments, the cells produced and administered according to this disclosure differentiate into neurons, oligodendrocytes, and astrocytes, and as such reconstitute lost cellular elements of the injured brain and spinal cord. In some embodiments, implantation of the NPCs, OPCs and oligodendrocytes of this disclosure into diseased areas mediates structural regeneration and repair. This may include, without limitation reconstitution of brain tissues lost to stroke and injury. In addition, neural stem cells are highly migratory in perinatal brain and, as a result, may also be used to replete deficient or mutated enzymes in hereditary and metabolic diseases.

To date, most experimental therapeutic studies of neural stem and progenitor cell engraftment have been done using fetal or adult tissues as the sources of neural stem and progenitor cells. These approaches have required the constant acquisition of new fetal and adult tissues, from both animal and human donors. The latter is particularly problematic as a source, since human tissue-derived cells, whether of fetal or adult origin (Keyoung et al., "Specific Identification, Selection and Extraction of Neural Stem Cells from the Fetal Human Brain," *Nature Biotech.* 19:843-850 (2001); Pincus et al., "Fibroblast Growth Factor-2/Brain-Derived Neurotrophic Factor-Associated Maturation of New Neurons Generated from Adult Human Subependymal Cells," *Ann. Neurol.* 43:576-585 (1998); Roy et al., "Promoter-Targeted Selection and isolation of Neural Progenitor Cells from the Adult Human Ventricular Zone," *J. Neurosci. Res.* 59:321-331 (2000); and Roy et al., "In Vitro Neurogenesis by Progenitor Cells isolated from the Adult Human Hippocampus," *Nature Med.* 6:271-277 (2000), which are hereby incorporated by reference in their entireties), are difficult to obtain and more difficult to standardize and scale up. In contrast, the NPCs, OPCs and oligodendrocytes produced using the methods of the present disclosure permit the ready acquisition, scalable expansion and directed differentiation of neural stem and progenitor cells.

Moreover, according to the present disclosure autologous NPCs, OPCs and oligodendrocytes may be used in some embodiments. Alternatively, heterologous NPCs, OPCs and oligodendrocytes may be used in any of the methods of treatment of this disclosure. Neural stem and progenitor cells derived from ES cells, of both murine and human origin, have already been found to be capable of both remyelination, in the case of ES-derived glial and oligodendrocytes, and dopaminergic replenishment in experimental Parkinson's disease, in the case of ES-derived midbrain dopaminergic neurons. By now achieving the purification of neural stem cells from ES cells culture, the present invention increases substantially both the reliability and safety of their use and may, therefore, Obviate the need for human tissue acquisition.

Another aspect of the disclosure features a method of treating a subject having a neurodegenerative condition, the method comprising administering to the patient postpartum-derived cells as described above, in an amount effective to treat the neurodegenerative condition. In certain embodiments, the neurodegenerative condition is an acute neurodegenerative condition, such as a brain trauma (focal or diffuse brain trauma), spinal cord trauma or peripheral nerve trauma e.g., resulting from physical or chemical burns, deep cuts or limb severance, cerebrovascular insufficiency. In other embodiments, it is a chronic or progressive neurodegenerative condition, such as Parkinson's disease, Alzheimer's disease, Huntington's disease, amyotrophic lateral sclerosis, tumor, or chronic peripheral nerve injury, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Sträussler-Scheinker disease, Kuru and fatal familial insomnia).

In still other embodiments, it is a disease associated with demyelination, such as multiple sclerosis, acute disseminated encephalomyelitis, neuromyelitis optica, transverse myelitis, chronic inflammatory demyelinating polyneuropathy, Guillain-Barré syndrome, central pontine myelinosis, inherited demyelinating diseases such as leukodystrophy, Charcot-Marie-Tooth disease and Canavan disease.

In certain embodiments, the iPSCs, ESCs, NPCs, OPCs, oligodendrocytes of the present disclosure can be administered separately, together or in combinations of two or more. In still other embodiments, the cells are administered with at least one other agent, such as a drug for neural therapy, or another beneficial adjunctive agent such as an anti-inflammatory agent, anti-apoptotic agents, antioxidant or growth factor.

In certain embodiments, the cells are administered at a pre-determined site in the central or peripheral nervous system of the patient. They can be administered by injection or infusion, or encapsulated within an implantable device, or by implantation of a matrix or scaffold containing the cells. Alternatively, it may comprise an implantable device in which the cells are encapsulated, or a matrix or scaffold containing the cells. The pharmaceutical composition may contain other materials such as natural biomaterials, for example, gelatin, collagen, carboxymethyl cellulose. Injectable delivery may use saline vehicles.

EXAMPLES

The invention is now described with reference to the following Examples. These Examples are provided for the purpose of illustration only, and the invention is not limited to these Examples, but rather encompasses all variations that are evident as a result of the teaching provided herein. The following table includes experimental conditions for use in some embodiments, including experimentally verified conditions. Any one of the parameters, ranges of the parameters or exemplary parameters from the table below or provided herein may be used with any other one of the parameters, ranges of the parameters or exemplary parameters in the table below or provided herein.

TABLE 1 oligodendrocyte differentiation

| | Parameter | | |
|---|---|---|---|
| | About 3-about 10 days Stage 1 | About 4-about 20 days Stage 2 | About 7-about 30 days Stage 3 |
| Starting Cells | iPSCs (or ESCs) | NPCs | OPCs |
| Culture Vessels | Culture Plate/flask | Culture Plate/flask, low attachment plate | Culture Plate/flask, low attachment plate |
| Coating | Matrigel (Thermo-Fisher)/PLO-Laminin (Sigma-Aldridge) | Matrigel (Thermo-Fisher)/PLO-Laminin (Sigma-Aldridge) | Matrigel (Thermo-Fisher)/PLO-Laminin (Sigma-Aldridge) |
| Dissociation | EDTA/Triple/Accutase | EDTA/Triple/Accutase | EDTA/Triple/Accutase |
| Medium Names and Main Components | MEMa, DMEM/F12, DMEM B27, N2, KSR, BSA/HSA, bFGF Ngn2 or Pax6 or Sox2 or Brn2 or FoxO combined or individual mRNA transfection SB431542, LDN193189, PD173074 are optionally added to enhance iPSC or ESC differentiation | DMEM/F12, DMEM, MEMa KSR, Ascorbic Acid, SAG, PDGF, HGF, IGF1, T3, Insulin, RA, B27, CAMP, Biotin Oligo2, NKX2.2, SOX10, Oligo1 combined or individual mRNA transfection | DMEM/F12, DMEM, MEMa KSR, Ascorbic Acid, N2, B27, Biotin, CAMP, T3, Insulin |
| Seeding Density (For 6-well Plate) | $1 \times 10^5 - 1 \times 10^6$ cells per well | $1 \times 10^5 - 1 \times 10^6$ cells per well | $1 \times 10^5 - 1 \times 10^6$ cells per well |
| Oxygen | Normal or low (e.g. 5% or 3%) Oxygen | Normal or low Oxygen | Normal or low Oxygen |

Another aspect of the invention features a pharmaceutical composition for treating a patient having a neurodegenerative condition, comprising one or more of the cell types of the disclosure and a pharmaceutically acceptable carrier. The neurodegenerative condition to be treated may be an acute neurodegenerative condition, or it may be a chronic or progressive condition.

In certain embodiments, the pharmaceutical composition comprises at least one other agent, such as a drug for neural therapy, or another beneficial adjunctive agent such as an anti-inflammatory agent, anti-apoptotic agents, antioxidant or growth factor.

In certain embodiments, the pharmaceutical composition is formulated for administration by injection or infusion.

In some embodiments, the number of cells used for seeding may be, for example, about ($7.1250 \times 10^4$, $1.187500 \times 10^6$, $2.375000 \times 10^6$, $4.750000 \times 10^6$, $7.125000 \times 10^6$, $9.500000 \times 10^6$, $1.1875000 \times 10^7$, or $1.4250000 \times 10^7$) or any number of cells between any two of the recited number of cells. The seeding density as number of cells/cm$^2$ may be determined for any culture vessel by dividing the number of cells by the growth area of the culture vessel (see Table 2), for example, using a 6-well plate with a growth area of 9.5 cm$^2$ the seeding density would be about ($0.75 \times 10^5$, $1 \times 10^5$, $1.25 \times 10^5$, $2.50 \times 10^5$, $5.00 \times 10^5$, $7.50 \times 10^5$, $1 \times 10^6$, $1.25 \times 10^6$, or $1.5 \times 10^6$ cells/cm$^2$) per six-well plate, or any density between any two of the recited densities. Thus, the cell density needed for any culture vessel can be determined in a similar manner.

TABLE 2

Growth Area of Common Culture Vessels

| | Growth Area (cm²) | Media Volume (ml) | Maximum Volume (ml) |
|---|---|---|---|
| Culture Plates | | | |
| 6 well | 9.5 | 9.5 | 1.9-2.0 |
| 12 well | 3.8 | 3.8 | 0.76-1.14 |
| 24 well | 1.9 | 1.9 | 0.38-0.57 |
| 48 well | 0.95 | 0.95 | 0.19-0.28 |
| 96 well | 0.32 | 0.32 | 0.1-0.2 |
| 24 well Flasks | 1.9 | 1.9 | 0.38-0.57 |
| T25 | 25 | 25 | 5-7.5 |
| T75 | 75 | 75 | 15-22.5 |
| T150 | 150 | 150 | 30-45 |

In some embodiments the oxygen concentration may be for example, about (2, 2.25, 2.5, 2.75, 3.0, 3.25, 3.5, 3.75, 4.0, 4.25, 4.5, 4.75, 5, 5.25, 5.5, 5.75, or 6.0%) oxygen or any range between any two of the recited percentages.

Example 1: Generating Neural Progenitor Cells from iPSCs iPSCs were plated into standard size 6-well cell culture plates (about 9.5 cm² growth area/well) or standard size 12-well cell culture plates (about 3.8 cm² growth area/well) to begin differentiation. Other-sized culture vessels are optionally applicable as well and sometimes may be more preferred over 6-well or 12-well plates because of higher efficiency of the use of reagents and time. Applicant has confirmed that the disclosed methods can be used in other-sized culture vessels.

In a 6-well plate, cells of a population size from about $1 \times 10^5$ to about $1 \times 10^6$ per well have been successfully used. iPSCs were considered ready for differentiation when there were enough typical iPSCs colonies with sharp well-defined edges, where the cells are compact, and colonies were not overgrown. The quality of iPSCs of the present invention produced using these criteria proved to be critical for differentiation when the iPSC lines of the present invention were compared with iPSC lines that were produced by others using other methods, even though the Applicant were able to successfully derive iPSCs made by other workers using non-mRNA methods such as the NCL2 iPSC line made by NIH/Lonza (data not shown). On the other hand, the disclosed technology could also be applied at any stage during the process, for example, start with NPC to derive towards OPC, astrocytes, or other glial cells; or start with OPC to derive towards astrocytes or other glial cells. In one exemplary experiment, Applicant used primary NPCs isolated from donated tissues and further differentiated them into OPCs and oligodendrocytes using the same protocol and in parallel to NPCs directly differentiated from iPSCs. The results using two different sources of NPCs were generally similar, with the iPSC-derived NPCs having slightly higher efficiency, and higher tendency to form spheres when Applicant tried to grow cells in suspension at that stage (data not shown).

iPSCs at this stage were induced to differentiate into ectoderm lineage cells. We discovered that suspension culture systems were very useful for scaling up at this stage even though most current protocols for differentiation prefer to use attached monolayer cells. We found that iPSCs grown in suspension for induction were more resistant to chemical toxicity and were easier to re-plate in later stages. We used Ultra-Low Attachment plates (Sigma-Aldrich) or other low attachment plates to encourage iPSC suspension cell growth when the suspension culturing route was selected for a particular differentiation "run".

When iPS cells need to be passaged, it was important to dissociate iPSC colonies with a protocol that caused low cytotoxicity and resulted in more small clusters of iPSCs, which can form spheres quickly if suspension culture is desired. iPSCs were dissociated using TripLE™ (ThermoFisher), Accutase (Life Technology), or EDTA by dissociating with EDTA of about 0.1 mM, sometimes about 0.5 mM, or about 1 mM in DPBS (Fisher Scientific), at about 37° C. for 5 minutes. Various dissociation times were used successfully, including about 1 to about 2 minutes, and sometimes about 10 to about 20 minutes for this step. In some embodiments the dissociation times may be about (1, 2, 3, 4, 5, 6, 7, 8, 9, 10, 11, 12, 13, 14, 15, 16, 17, 18, 19, 20), or any range of time between any two of the recited times.

For medium, we tested MEMa or DMEM/F12 or DMEM+B27 with 5% KSR and were able to achieve the results as desired at this stage of differentiation. Medium supplement N2, BSA or HAS, and bFGF were also used in the medium depending what base medium was used at this stage. iPSCs were then induced to leave the pluripotent stage and differentiate towards ectoderm as an optional step by the presence of SB431542, LDN193189, PD173074 of, for example, about (5 mM, 6 mM, 7 mM, 8 mM, 9 mM, 10 mM) or any range between any two of the recited concentrations. LDN-193189 is a highly potent small molecule inhibitor of bone morphogenetic protein (BMP) type I receptors ALK2 and ALK3. LDN193189 is a selective transcriptional activity morphogenetic protein (BMP) type I receptors inhibitor. It inhibits activin receptor-like kinase-2 (ALK2) and ALK3. SB431542 is a selective and potent inhibitor of the TGF-β/Activin/NODAL pathway and is a potent and selective inhibitor of ALKS. PD173074 is a potent FGFR1 inhibitor and also inhibits VEGFR2. In other embodiments other inhibitors of these pathways may also be used.

Figure 1:
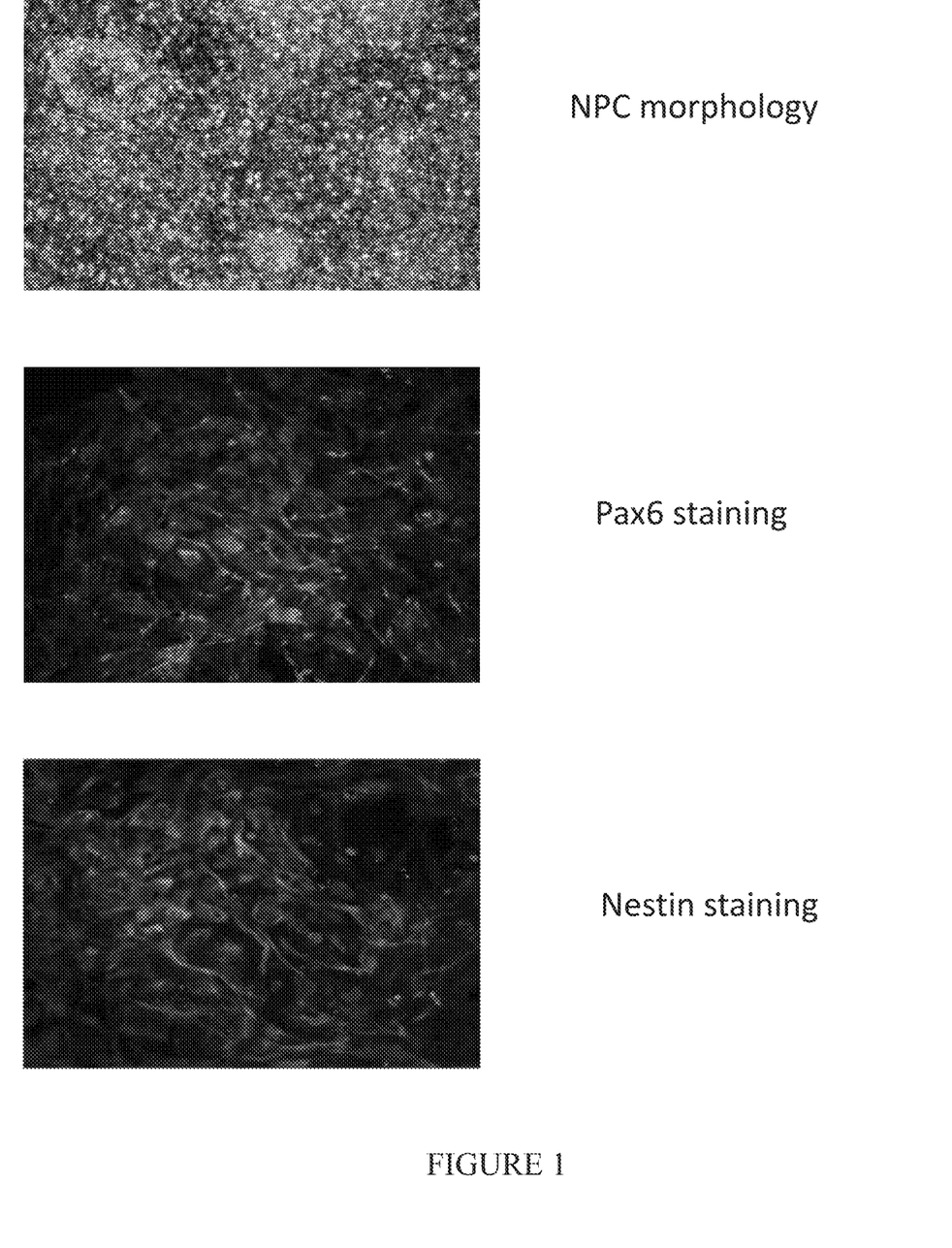
FIG. 1. Exemplary embodiment of neural progenitor cell (NPC) induction.

In one experiment, cells were then transfected with Ngn2, Pax6, Sox2, Brn2, FoxO (one or more members of the subclass) mRNA individually or in combinations at a dose of 20 ng per well using a six-well plate with Stemgent Transfection Reagent (Stemgent) or other transfection reagents. The mRNA dose can be proportionally adjusted, based on the area of the culture vessel or the volume of the culture media amount when using other types of culture plates. This transfection was repeated for 3, 4, 5 or 6 times, sometimes at a dose of mRNA about 10 times higher, using Stemgent Transfection Reagent or other commercially available transfection reagents. Repeated transfections for the Examples disclosed herein can be performed around 24 hours plus or minus 2 to 3 hours after the first transfection, or overnight from the first transfection or at about (6-24 hours, 7-24 hours, 8-24 hours, 9-24 hours, 10-24 hours, 11-24 hours, 12-24 hours, 13-24 hours, 14-24 hours, 15-24 hours, 16-24 hours, 17-24 hours, 18-24 hours, 19-24 hours 20-24 hours, 21-24 hours, 22-24 hours), or all ranges in between two recited time points after the first transfection. Cells at this stage showed morphology that were closer to neural progenitor cells than mesenchymal cells, but these NPCs produced by expression of TFs, compared to NPCs produced by other, mostly chemical-based methods, appeared to give higher yield of cells in the oligodendrocyte pathway. The NPCs at this stage were Pax6 positive by antibody staining, demonstrating their identity in the neural progenitor lineage (FIG. 1). mRNA DNA, and protein sequences for Ngn2, Pax6, Sox2, Brn2, FoxO are known in the art, for example, GenBank. Methods for preparing mRNA for transfection for use in the methods described herein are known in the art, for example, U.S. patent application Ser. Nos. 13/893,166 and 14/292,317; (the contents hereby incorporated by reference).

Example 2: Generating Oligodendrocyte Progenitor Cells from Neural Progenitor Cells Neural progenitor cells, or NPCs, were plated on commercial cell culture vessels. 6-well plates were used in experiments shown in FIG. 2, but other well sizes are applicable. Plates were pre-coated with Matrigel (BD Biosciences) and PLO-Laminin, about $1 \times 10^5$-$1 \times 10^6$ cells were then plated in DMEM/F12 or DMEM or MEM3 supplemented with KSR as well as Ascorbic Acid, SAG, PDGF, HGF, IGF1, T3, Insulin, RA, B27, CAMP, biotin at commonly used concentrations. NPCs produced by using chemical-based protocols commonly known in the field were also used to generate OPCs in the following steps, it was observed that NPCs produced by introducing TF activities produced more and far better OPCs.

Figure 2:
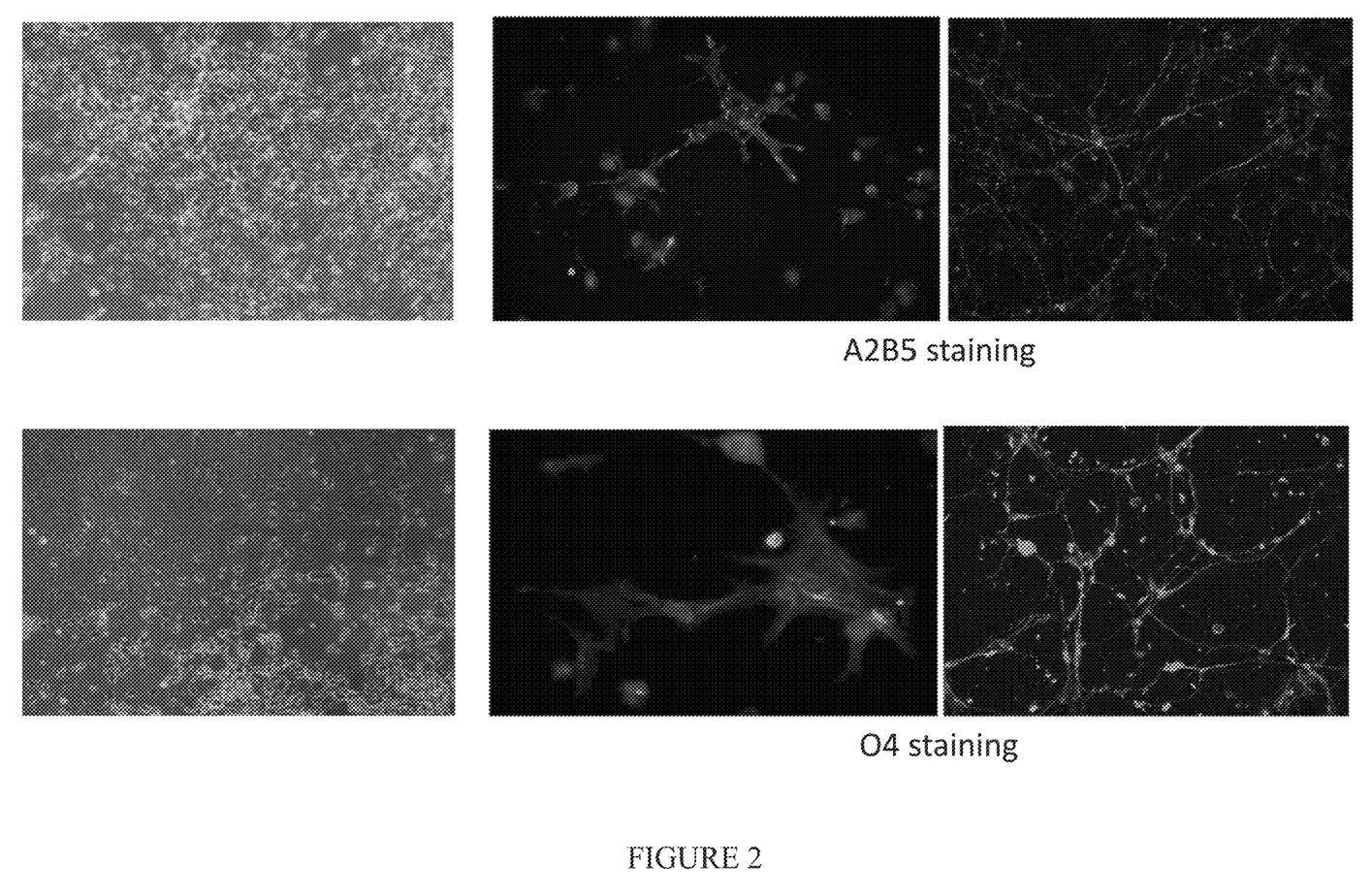
FIG. 2. Exemplary embodiment of oligodendrocyte progenitor cell (OPC) induction.

In one experiment, cells were then transfected with one or various combinations of Oligo2, NKX2.2, SOX10, and Oligo1 mRNA individually or in combinations at a dose of about 20 ng per well/per cell-fate factor with Stemgent Transfection Reagent (Stemgent) in culture medium, and repeated at around 24 hours for 2, 3, 4 or more times, at doses as low as about 10 ng and as high as about 200 ng per well, using Stemgent Transfection Reagent or other commercially available transfection reagents. The cells at this stage appear to change from the typical morphology of NPCs to OPCs and stained positive for A2B5 and O4 (FIG. 2).

Example 3: Generating Oligodendrocytes from OPCs

Figure 3:
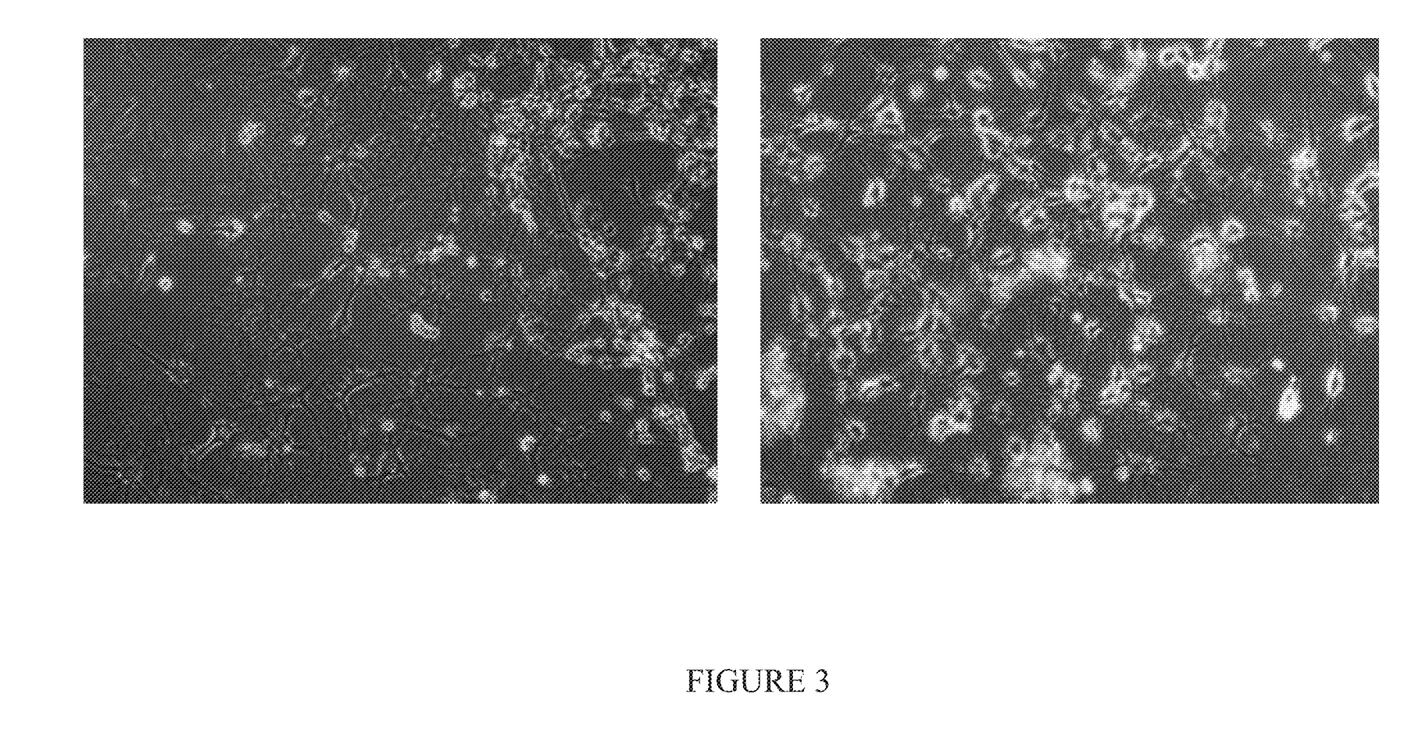
FIG. 3. Exemplary embodiment of oligodendrocyte induction.

Oligodendrocyte progenitor cells were cultured in 6-well or other plates pre-coated with Matrigel (BD Biosciences) and/or PLO-Lamnin in DMEM/F12 or MEMa or DMEM B27. Other similar attachment cell culture medium is also suitable for use. The medium was typically supplemented with Ascorbic Acid, N2, B27, biotin, CAMP, T3, insulin, and KSR at commonly used concentrations. The cells were cultured for about 1 week, sometimes about 2, about 3, or even about 4 weeks during which time mature-looking oligodendrocytes appeared and migrate out from the OPC clusters then spread into the space, where they formed increasing number of tree branch-looking processes (FIG. 3).

Example 4: During Further Culturing, Oligodendrocytes Form New Clusters

Figure 4:
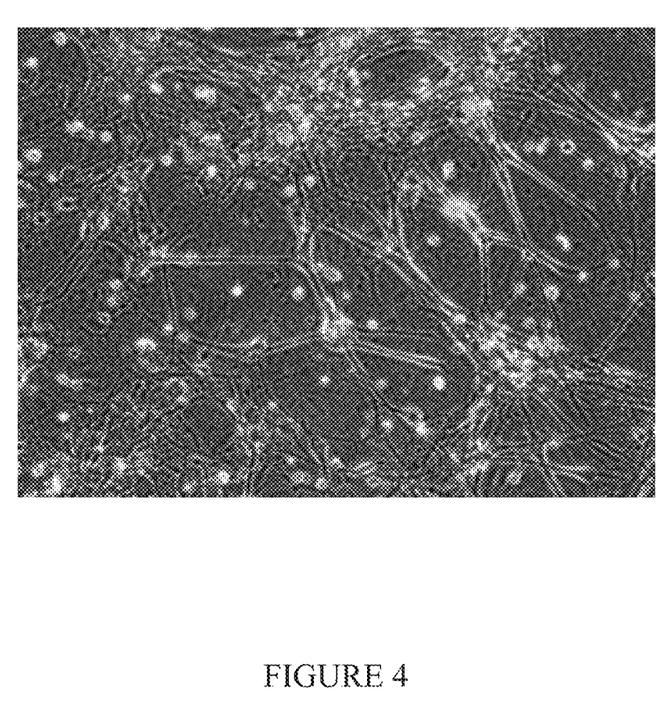
FIG. 4. Exemplary embodiment of oligodendrocyte further culturing and maturation.

When oligodendrocyte-like cells from stage 2 were allowed to continue to grow for about 1 week to about 4 more weeks, or even longer, they form new clusters with overlapping processes, somewhat mimicking in vivo sheath formation (FIG. 4).

Figure 5:
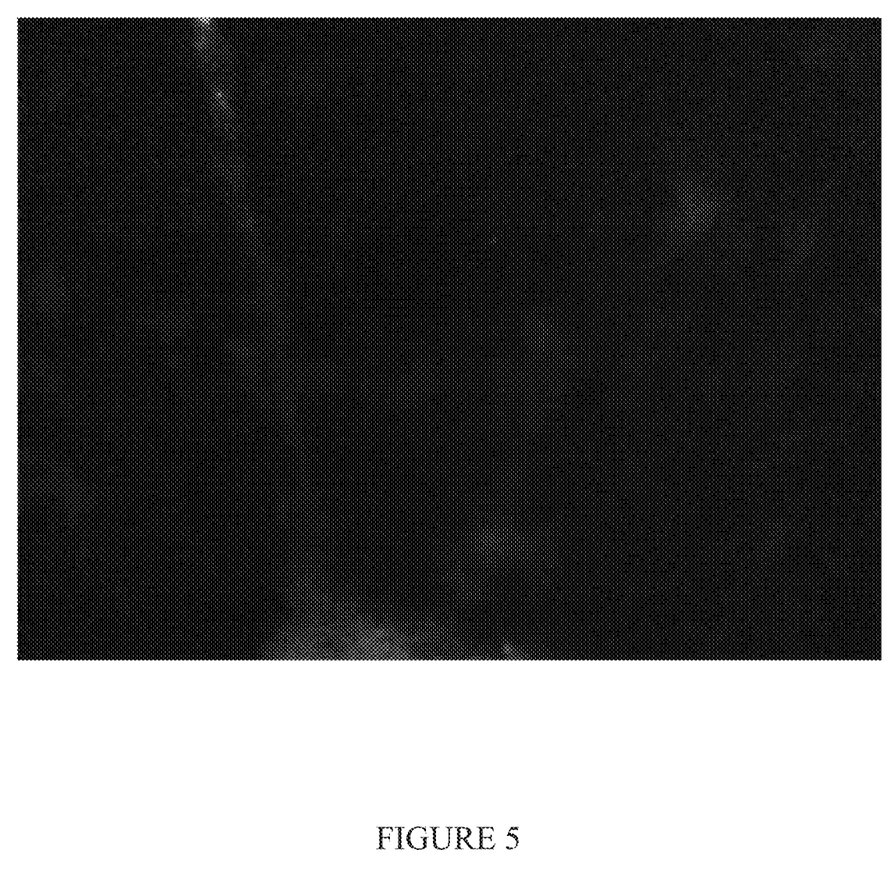
FIG. 5. Exemplary embodiment of oligodendrocyte derived from human iPSCs show specific cell markers.

Example 5: Exemplary Embodiment of Oligodendrocyte Derived from Human iPSCs Show Specific Cell Markers To demonstrate that oligodendrocytes that were derived from human pluripotent stem cells were mature oligodendrocytes, they were removed from differentiation culture plates by chemical or physical means into spheres, fixed, and stained with anti-MBP antibodies. It appeared that all cells so produced stained positive for MBP, a commonly known mature oligodendrocyte marker (FIG. 5).

Example 6: iPSC-Derived Oligodendrocytes Function in Animal Models

To further test the functions of the mature oligodendrocyte produced according to the present invention, the cord repair function of the iPSC-derived oligodendrocytes could be tested in spinal cord injury rat models such as those described by Mark Tuszynski's group and others. Oligodendrocytes could be delivered as cells, cell sheet, cell clusters, as the lone cell type or in combination with other cells such as OPCs, or NPCs. OPCs derived from iPSCs by the disclosed method will also be tested as a therapy candidate to treat spinal cord injuries or or other central neural diseases and conditions. In another embodiment, oligodendrocytes, OPCs, NPCs or their combinations could be presented on hydrogels, in some cases in the presence of cell trophic factors such as BDNF, NGF, etc.

Non-human Primate Models such as monkeys and chimpanzees could also be used for testing human cells such as oligodendrocytes of the central neuronal system in terms of safety and efficacy with immune suppressor, or with corresponding non-human-primate iPSCs derived NPCs, OPCs, or oligodendrocytes using essentially the same methods disclosed herein.

Example 7: iPSC-Derived Oligodendrocytes in Treating Human Patients with Spinal Cord Injuries or Other Central Neural Diseases and Conditions Clinical trials using human iPSC-derived oligodendrocytes, OPCs, NPCs, neurons or a combination of the above using the disclosed protocols adapted to suit under cGMP procedures will be dosed according to animal studies with reference to other cell therapies. The manufactured cells can be delivered to spinal cord, or possibly other parts of the human central nervous system such as the brain.

Figure 6:
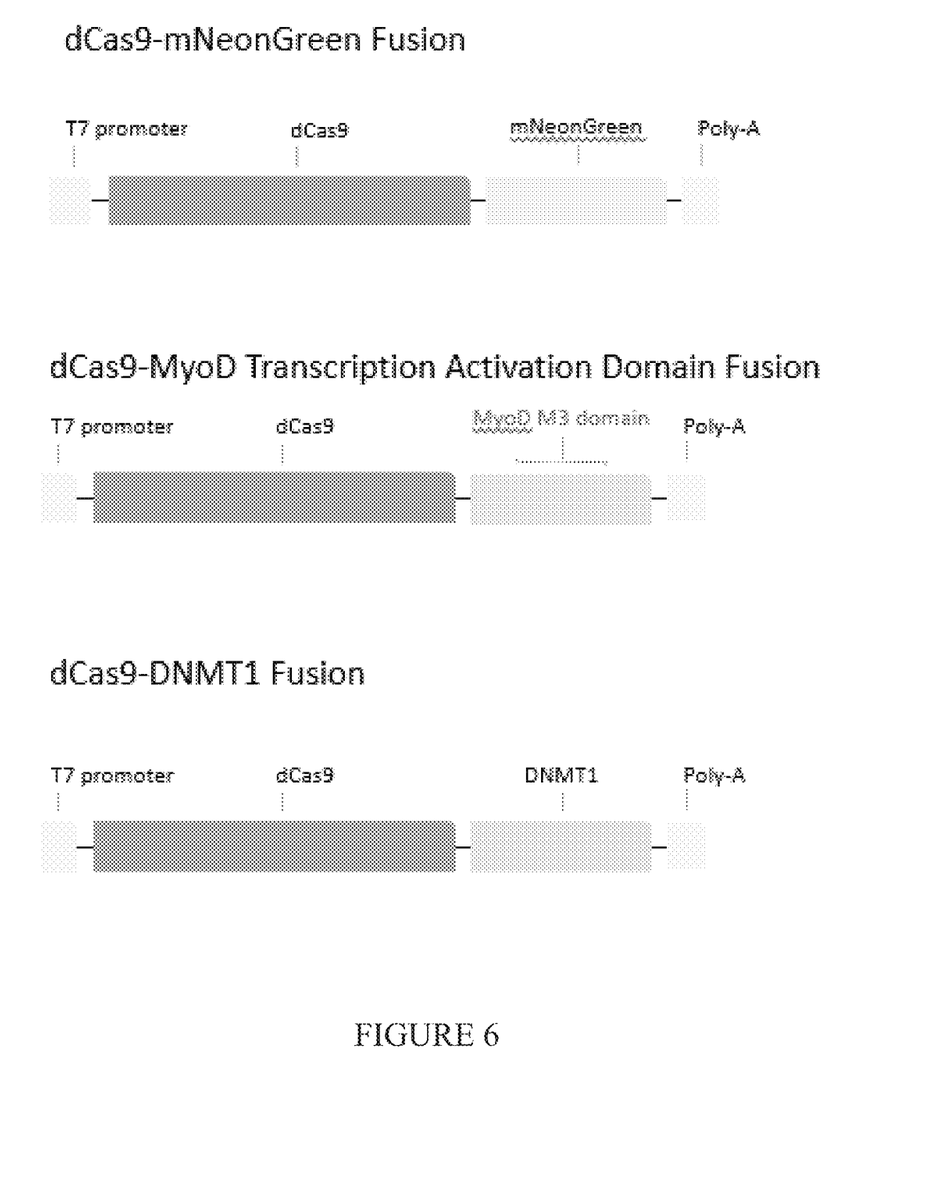
FIG. 6. Exemplary embodiment of using CRISPR-Cas-based gene expression regulators to achieve different key TF mRNA levels inside the cells being differentiated.

Example 8: Using CRISPR-Cas9 System for Driving Key Genes' Expression Thereby Using mRNAs Produced Through In-Cell Transcription for Cell Fate Decisions As shown in FIG. 6, a nuclease-deactivated version of Cas9, dCas9, was linked to a fluorescent protein, mNeonGreen (Allele Biotechnology), as an example to show that a functional protein could be localized to region of interest within a genome through Cas9 fusion directed by a gRNA. The same strategy can be applied to function domains, proteins, peptides, etc., in order to drive gene expression (i.e. mRNA production inside the cell to be cell fate-decided), an example is MyoD transcription activation domain shown in FIG. 6; other examples could be VP16 and many other such domains. When such a transcription activation fusion Cas9-fusion protein is placed in regions through gRNA that turn on the key TFs, such as Ngn2 or Pax6 or Sox2 or Brn2 or FoxO or Oligo2 or NKX2.2 or SOX10, the results of transfecting in vitro transcribed mRNA can be achieved. The same strategy can be applied to enzymatically active domains or proteins that would influence gene expression by epigenetically modifying particular region(s) on a chromosome, such as using DNA (cytosine-5)-methyltransferase 1, or DMNT1. Nucleotide converting enzymes fused to Cas9 could be used to switch a particular nucleotide to another nucleotide, thereby changing the encoded protein or causing early termination of a protein production. This way a cell's gene expression profile can be changed and cell fate determined when the changed genes are key TFs such as the genes listed above and other genes, following the general strategy disclosed in this application.

Nuclease deactivated Cas9 is known in the art as well as methods to fuse transcription activation domains and target using guide RNA. (Didovyk et al., *Current Opinion in Biotechnology* (2016), 40:177-184) (the contents incorporated herein by reference). Preparation of guide RNA sequences targeting cell-fate factor promoters can be prepared as in Balboa et al., *Stem Cell Reports* (2015) 5:448-459 (the contents incorporated herein by reference).

We claim:

1. A method for generating oligodendrocyte progenitor cells (OPCs) from neural progenitor cells (NPCs) said method comprising:
    a) plating NPCs on coated cell culture vessels in medium;
    b) transfecting the cells of step a) two or more times with mRNA encoding one or more cell-fate factors, wherein the mRNA encoding the cell-fate factors consists of oligodendrocyte transcription factor 1 (Oligo1) mRNA, or consists of a combination of Oligo1 mRNA and at least one mRNA selected from oligodendrocyte transcription factor 2 (Oligo2) mRNA, NK2 Homeobox 2-2 (NKX2.2) mRNA, and SRY-box transcription factor 10 (SOX10) mRNA to differentiate neural progenitor cells to oligodendrocyte progenitor cells; and
    c) culturing the cells of step b) until the morphology of the NPCs change to the morphology of OPCs.

2. The method of claim 1, wherein the NPCs of step a) are seeded using about 70,000 cells to about 14,000,000 cells per culture flask or culture well-plate.

3. The method of claim 1, wherein a six-well culture plate is used and the dose for the transfection in step b) is about 20 ng/per cell-fate factor.

4. The method of claim 1, wherein after the first transfection, the transfection is repeated at least two more times.

5. The method of claim 1, wherein the culture conditions of steps a)-c) are in an oxygen concentration of about 2% to about 6%.

6. The method of claim 1, wherein the cell culture vessels are coated with basement membrane matrix and PLO-Laminin.

7. The method of claim 1, wherein the medium used for steps a)-c) is selected from the group consisting of DMEM/F12, DMEM, and MEMa.

8. The method of claim 7, wherein the medium is supplemented with one or more of KnockOut Serum Replacement (KSR), ascorbic acid, sonic hedgehog agonist (SAG), platelet-derived growth factor (PDGF), hepatocyte growth factor (HGF), insulin-like growth factor-1 (IGF1), triiodothyronine (T3), insulin, retinoic acid (RA), B27, cyclic adenosine monophosphate (CAMP), and biotin.

9. The method of claim 1, wherein the cells of step c) are cultured for about 4 to about 20 days.

10. The method of claim 1, wherein the mRNA encoding one or more cell-fate factors consists of Oligo1 and Oligo2 mRNA.

11. The method of claim 1, wherein the mRNA encoding one or more cell-fate factors consists of Oligo1 and NKX2.2 mRNA.

12. The method of claim 1, wherein the mRNA encoding one or more cell-fate factors consists of Oligo1 and SOX10 mRNA.

13. The method of claim 1, wherein the mRNA encoding one or more cell-fate factors consists of Oligo1 mRNA.

14. The method of claim 1, wherein the mRNA encoding one or more cell-fate factors comprises consists of Oligo2, NKX2.2, SOX10, and Oligo1 mRNA.

* * * * *